(12) United States Patent
Bordoloi et al.

(10) Patent No.: US 9,468,914 B2
(45) Date of Patent: Oct. 18, 2016

(54) PROCESS FOR THE PREPARATION OF PHOSPHOROUS CONTAINING MESOPOROUS ALUMINA CATALYST FOR SELECTIVE DEHYDRATION OF METHANOL TO DIMETHYL ETHER

(71) Applicant: COUNCIL OF SCIENTIFIC & INDUSTRIAL RESEARCH, New Delhi (IN)

(72) Inventors: Ankur Bordoloi, Dehradun (IN); Reena Goyal, Dehradun (IN); Subhasis Das, Dehradun (IN); Rajib Kumar Singha, Dehradun (IN); Chandrashekar Pendem, Dehradun (IN); Laxmi Narayan Sivakumar Konathala, Dehradun (IN); Rajaram Bal, Dehradun (IN); Sandeep Saran, Dehradun (IN); Madhukar Onkarnath Garg, Dehradun (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/634,200

(22) Filed: Feb. 27, 2015

(65) Prior Publication Data
US 2015/0336086 A1    Nov. 26, 2015

(30) Foreign Application Priority Data
May 23, 2014   (IN) .......................... 1364/DEL/2014

(51) Int. Cl.
*B01J 27/16*   (2006.01)
*B01J 37/04*   (2006.01)
*B01J 37/08*   (2006.01)
*C07C 41/09*   (2006.01)

(52) U.S. Cl.
CPC ................. *B01J 27/16* (2013.01); *B01J 37/04* (2013.01); *B01J 37/08* (2013.01); *C07C 41/09* (2013.01)

(58) Field of Classification Search
None
See application file for complete search history.

(56) References Cited

U.S. PATENT DOCUMENTS

| 6,027,706 A * | 2/2000 | Pinnavaia ............... C01B 37/00 |
| | | 423/600 |
| 2012/0088654 A1* | 4/2012 | Wang .................. B01J 27/1804 |
| | | 502/164 |

FOREIGN PATENT DOCUMENTS

| CN | 101829552 A | * 9/2010 |
| CN | 102476819 A | * 5/2012 |
| EP | 0 099 676 | 2/1984 |
| JP | 59-16845 | 1/1984 |
| JP | 59-42333 | 3/1984 |

OTHER PUBLICATIONS

F. Yaripour et al.; "Catalytic Dehydration of Methanol to Dimethyl Either Catalyzed by Aluminum Phosphate Catalysts"; Energy & Fuels; vol. 23; 2009; pp. 1896-1900.
G.R. Moradi et al.; "Catalytic Dehydration of Methanol to Dimethyl Ether Over Mordenite Catalysts"; Fuel Processing Technology; vol. 91; 2010; pp. 461-468.
Grigore Bozga et al.; "Dimethyl Ether Synthesis Catalysts, Processes and Reactors"; Recent Patents on Catalysis; 2013; pp. 68-81.

\* cited by examiner

*Primary Examiner* — Rosalynd Keys
(74) *Attorney, Agent, or Firm* — Blank Rome LLP

(57) ABSTRACT

The present invention provides an improved process for the preparation of phosphorous containing mesoporous alumina catalyst for selective dehydration of methanol to dimethyl ether. The process provides a single step selective vapor phase dehydration of methanol to produce dimethyl ether over phosphorous containing mesoporous alumina (P/Al2O3) catalyst at a temperature in the range of 150-350° C. The process provides methanol conversion of 45-100% with a selectivity of the DME up to 100%.

6 Claims, 4 Drawing Sheets

PROCESS FOR THE PREPARATION OF PHOSPHOROUS CONTAINING MESOPOROUS ALUMINA CATALYST FOR SELECTIVE DEHYDRATION OF METHANOL TO DIMETHYL ETHER

CROSS-REFERENCE TO RELATED APPLICATION

This application claims the benefit of co-pending Indian Patent Application No. 1364/DEL/2014 filed May 23, 2014, the disclosure of which is incorporated herein by reference in its entirety.

FIELD OF INVENTION

The present invention relates to an improved process for the preparation of phosphorous containing mesoporous alumina catalyst for selective dehydration of methanol to dimethyl ether. Particularly, the present invention relates to vapour phase dehydration of methanol to dimethyl ether (DME). More particularly, the present invention relates to a process for the selective dehydration of methanol to dimethyl ether at atmospheric pressure with very high conversion and selectivity over phosphorous containing mesoporous alumina ($P/Al_2O_3$).

BACKGROUND OF THE INVENTION

The dual challenges of climatic change and depletion of oil reserves presents modern societies with a conundrum. Many of the alternatives to oil derived fuels produce higher carbon emissions, with associated costs to the environment and, if carbon emissions are priced, to the consumer. The early identification and development of solutions to this conundrum will allow for alternative to be introduced in a planned manner, thus avoiding disruptive change. In this application, we propose to explore the use of dimethyl ether (DME) as means of addressing this challenge. DME holds promise as a fuel is that can assist in the transition to a low carbon emissions future. In the short to medium term DME can be produced from natural gas (NG), with well-to-wheel emissions comparable with those of conventional fuels. An attraction of the introduction of DME as a fuel is that the infrastructure and technologies developed for its use now will position societies well for the future. DME is an ideal fuel for a range of stationary and mobile applications. It can be used in place of, or blended with liquefied petroleum gas (LPG), and is an excellent diesel fuel. In each case it produces significantly less pollution upon combustion than its conventional counterpart. Moreover, Dimethyl ether (DME) has been recently proved as a clean fuel because of its wide range of applicability's in industry such as aerosol propellant, in shaving cream, to replace ozone depleting chlorofluorocarbons in refrigerators. It would soon be able to replace conventional diesel fuel because of its thermal efficiencies equal to diesel fuel, high anti knocking property, low NOx emission. Secondly, it does not corrode the metal and less toxic for human beings. So methanol dehydration to DME production is development of an economic process. DME can be synthesized from two ways (1) directly from syngas (mixture of CO and $H_2$) over a hybrid catalyst through a two-step process hence it is energy consuming. Moreover the outcome product stream has lots of byproduct which reduces selectivity of DME. (2) Other process is methanol dehydration to DME through single step process.

The dehydration of methanol to DME is an exothermic process hence it follows a degree of conversion at reaction temperature as soon as possible. From the kinetic point of view, a minimum reaction temperature is required to ensure sufficient reaction rates. Extensive studies have been carried out on methanol dehydration to DME with different type of solid acid catalyst. The solid acid catalyst used for methanol to DME preparation includes gamma alumina (Japanese patent Kokai 1984-16845) silica-alumina (Japanese Patent Kokai 1984-42333) having hydrophilic surface. So as the reaction precedes catalyst get deactivated soon due to rapid blockage of activated site. However γ-alumina delivers high methanol conversion but irreversible deactivation desiccates for its industrial uses. The dehydration process of methanol to DME is acid catalyzed reaction, however, with high acidity of catalyst DME selectivity substantially decreases due to formation of hydrocarbons. Moreover, it is very difficult to precede catalytic dehydration step with weak acidity. This problem can be overcome by synthesis of catalyst with moderate acidity with significantly high surface area.

Reference can be made to the U.S. Pat. No. 8,304,582B2 wherein Zheng Li, et al. provided a one-step catalytic process of dehydration of methanol for the production of DME using silica aluminum phosphate catalyst. But the maximum conversion for methanol reaches to 86.06 at 360° C. and DME selectivity up to 96.78%. But the uses of excess pressure (up to 1500 KPa) reduce the life time of Si—Al—P catalyst.

Reference can be made to U.S. patent US 2011/0065963 A1 by Xiangbo Guo, et al. In their patent application, they claimed Beta-zeolites, and SAPO-molecular sieves catalyst for dehydration of methanol at ≤180-500° C. The main drawback of this process is the relative low conversion of methanol (only 80%). Furthermore, 500° C. is too high for methanol dehydration and at this temp coke deposition will favor rather than methanol dehydration. So life time of the catalyst have to be addressed.

Reference can be made to U.S. Pat. No. 5,750,799A in which Christiaan P. van Dijk and his coworkers disclose a process of DME Production and its recovery from methanol. But, the conversion they have addressed is only 76% whereas in presence of more amount of water it will further decreases.

Reference can be made to the European patent EP1597225 A4 by Jin Hwan Bang et al. in which they developed one step Process for preparing DME from methanol using hydrophobic zeolite having the $SiO_2/Al_2O_3$ ratio of 20-100. The reaction performed in a temperature ranges 150-350° C. at pressure ranges 1-100 bar and LHSV (liquid hourly space velocity) ranges 0.05-50 $h^{-1}$ where the outcome yield of DME is 91%. But such a high pressure is not viable for its industrial application, moreover the used of double packed catalyst system (which comprised one hydrophilic solid acid catalyst followed by hydrophobic MFI catalyst) makes the system more and more complex to tune for better conversion and yield.

Reference can be made to the Energy & Fuels 2009, 23, 1896-1900; wherein F. Yaripour et al. reported how phosphorus concentration affects methanol to DME yield over $AlPO_4$ as catalyst. Under the reported process 81.69% DME yield at 300° C. has been achieved with $AlPO_4$ catalyst. But only 81% methanol conversion can be achieved at 300° C.

Reference may also be made to Recent Patents on Catalysis, 2013, 2, 68-81, in which DME synthesis was carried out by two step process using CO and $H_2$ as starting material by copper dispersed on metal oxides. A product selectivity of ≥91% was achieved over CuO, ZnO and $Al_2O_3$ in different stoichiometric ratio. But main drawback is to obtain such a high CO conversion (maximum up to 95%) and DME selectivity pressure requirement of the reactor is 60 bar.

Reference may also be made to Fuel Processing Technology 91 (2010) 461-468 where methanol to dimethyl ether was carried out over various commercial mordenite and ion-exchanged catalysts by Moradi and his coworker. A conversion of 84.1 was obtained with 100% DME selectivity but GHSV and to achieve the conversion is too low.

Reference can also be made to US patent 20120220804A1 by Peter Mitschke et al. have reported a process for DME synthesis from crude methanol dehydration. However the crude methanol dehydration is an economic process but on increasing the content of carbonyl compound greater than 50 wt-ppm harmful trace components will appear in DME product.

OBJECTIVE OF THE INVENTION

The main object of the present invention is to provide an improved process for the preparation of phosphorous containing mesoporous alumina catalyst for selective dehydration of methanol to dimethyl ether.

Another objective of the present invention is to provide a process for dehydration of methanol to DME by vapour phase.

Still another objective of the present invention is to provide a process, which gives very high conversion of methanol with very high DME selectivity.

Yet other objective of the present invention is to provide a process which produces DME, which can be used as a fuel, particularly when it is blended with LPG can be used as an excellent diesel fuel.

Yet another object of the present invention is to provide a process which work under continuous process at atmospheric pressure for the production of DME from methanol.

Yet another object of the present invention is to provide a catalyst with a phosphorous containing mesoporous alumina ($P/Al_2O_3$) which can be prepared easily and also economical to produce DME by dehydration of methanol.

Yet other object of the present invention is to provide a process to deliver a simple catalyst which is reusable after simple washing.

SUMMARY OF THE INVENTION

Accordingly, the present invention provides an improved process for the preparation of phosphorus containing mesoporous Al2O3 catalyst, wherein said process comprising the steps of:
a) preparing a solution by mixing Aluminum isopropoxide in ethanol and adding phosphoric acid, nitric acid and ethanol into it to and stirring the solution for a period in the range of 9-11 hrs at 25° C. to 35° C.;
b) preparing a second solution by mixing Poly(ethylene glycol)-block-poly(propylene glycol)-block-poly(ethylene glycol) (P123) in ethanol;
c) mixing two solutions as obtained in steps (a) and (b) and stirring for a period in the range of 3-5 hrs at 25° C. to 35° C., followed by drying at a temperature in the range of 60°-150° C. for a period in the range of 3-48 hrs, subsequently calcining the catalyst at a temperature range of 700° C. for 2-8 hrs to obtain phosphorus containing mesoporous $Al_2O_3$ catalyst.

In an embodiment of the present invention, mol % ratio of Aluminium to phosphorus of the catalyst is in the range of 0.5 to 5%.

In one embodiment of the present invention, a process for the vapour phase selective dehydration of methanol to dimethyl ether (DME) over phosphorus containing mesoporous $Al_2O_3$ catalyst, wherein the process comprises placing said catalyst in between two quartz wool plugged in the center of the reactor and preheating the catalyst using helium at temperature in the range of 450° C.-600° C. for 2 hours, subsequently contacting methanol over the catalyst at 1 atmospheric pressure, at a temperature in the range of 150 to 350° C. for 1-50 h, at a liquid hourly space velocity (LHSV) in the range of 2 ml $g^{-1}$ $h^{-1}$ to 10 ml $g^{-1}$ $h^{-1}$ to obtain dimethyl ether (DME).

In another embodiment of the present invention, mol % ratio of Aluminium to Phosphorus of the catalyst is in the range of 0.5 to 5%.

In another embodiment of the present invention, conversion of methanol is in the range of 36 to 95%.

In another embodiment of the present invention, selectivity of the DME obtained in the range of 40 to 100%.

DETAILED DESCRIPTION OF THE INVENTION

The present invention discloses an improved process for the preparation of phosphorous containing mesoporous alumina catalyst for selective dehydration of methanol to dimethyl ether. The present invention further provides a process for the production of DME by vapour phase dehydration of methanol using phosphorous containing mesoporous alumina ($P/Al_2O_3$) as the catalyst in nitrogen atmosphere which involves the following steps:

1. Synthesis of phosphorous containing mesoporous alumina ($P/Al_2O_3$) catalyst using sol composition of Aluminum isopropoxide, Poly(ethylene glycol)-block-poly(propylene glycol)-block-poly(ethylene glycol) (P123), phosphoric acid and nitric acid in ethanol as solvent.
2. Synthesis of Aluminum phosphate catalyst using modified evaporation self-assembly method in ethanol medium using the solution composition of Aluminum isopropoxide, Poly(ethylene glycol)-block-poly(propylene glycol)-block-poly(ethylene glycol) (P123), in the molar ratio of Ethanol:Al:P123=1:0.02:0.0003
3. The mol % ratio of Al to P varied in the range of 0.5-5 mol percent.
4. The mixture was stir, drying followed by calcination at 400-800° C. for 4-6 h.

General Procedure for the Selective Dehydration of Methanol to DME

The dehydration of methanol was carried out in a fixed-bed down flow reactor at atmospheric pressure. Typically 150 mg of catalyst was placed in between two quartz wool plugged in the center of the 6 mm quartz reactor and dehydration of methanol was carried out in a temperature range of 200-350° C. The catalyst was preheated using He (10 ml/min) at 450° C. for 2 h before the reaction. The liquid hourly space velocity (LHSV) was varied between 2 ml $g^{-1}$ $h^{-1}$ to 10 ml $g^{-1}$ $h^{-1}$ with a constant He flow. The reaction products were analyzed using an online gas chromatography (Agilent 7890A) fitted with a TCD detector using Pora-Pack-Q and confirmed with standard.

The following examples are given by way of illustration of working of the invention in actual practice and should not be constructed to limit the scope of the present invention in any way.

Example—1

A typical synthesis procedure for the preparation of $P/Al_2O_3$ (P/Al=1) takes place as follows. Anhydrous Aluminum isopropoxide (4.1 g) was dissolved in 30 ml ethanol and 4 ml of concentrated nitric acid and phosphoric acid 1.2 ml was added into it. Finally 10 ml of ethanol was added again to the solution and kept for 10 h under vigorous stirring at 25° C. A second solution containing Poly(ethylene glycol)-block-poly(propylene glycol)-block-poly(ethylene glycol) (P123) 2 g was dissolved in 50 ml of ethanol. Two solutions were mixed and stirred for 3 hours for homogenation and kept for drying slowly at temperature 80° C. for a period 18 hours. The obtained material was calcined at 700° C. for 6 h.

Figure 1:
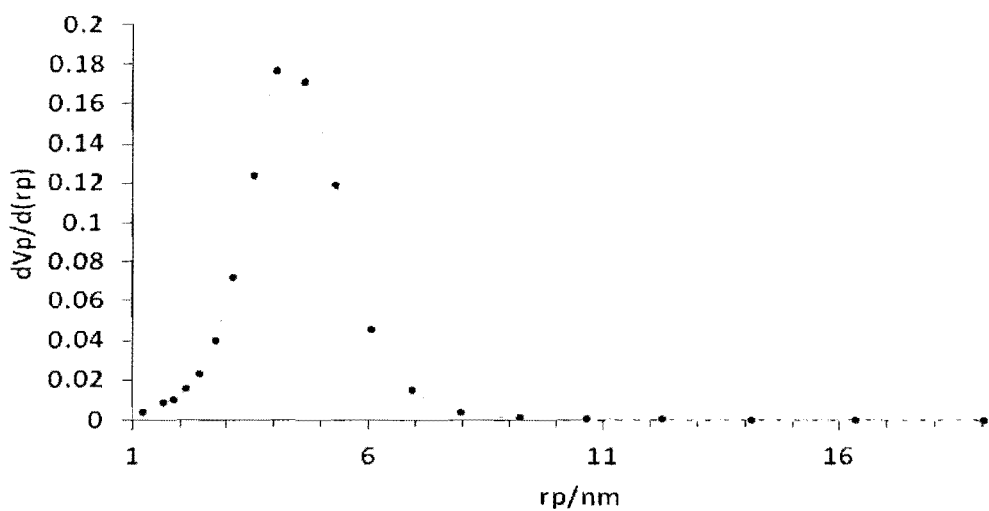
FIG. 1 shows BJH plot of mesoporous $P/Al_2O_3$ (P/Al=1) catalyst.
Figure 2:
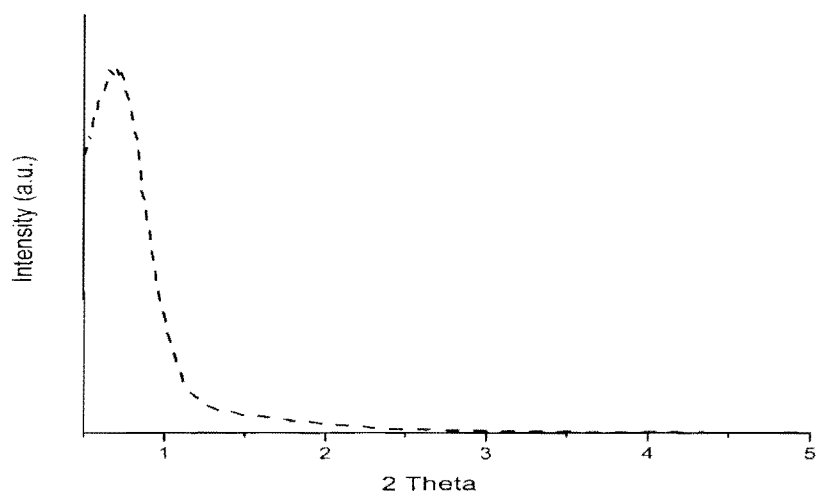
FIG. 2 X-ray Diffraction (XRD) of mesoporous $P/Al_2O_3$ catalyst.
Figure 3:
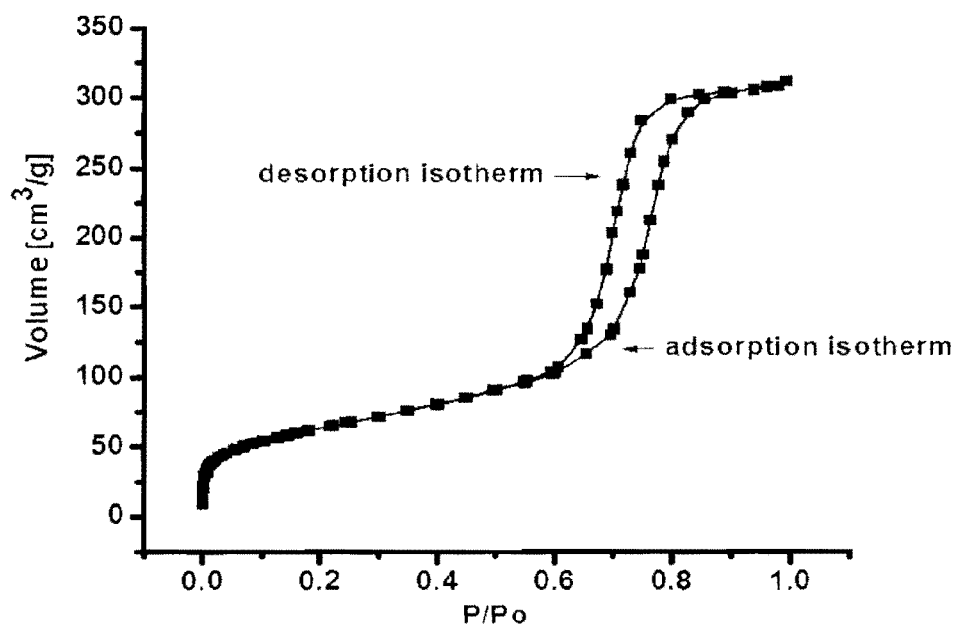
FIG. 3 shows Adsorption Desorption isotherm mesoporous P/Al2O3 (P/Al=1) catalyst.
Figure 4:
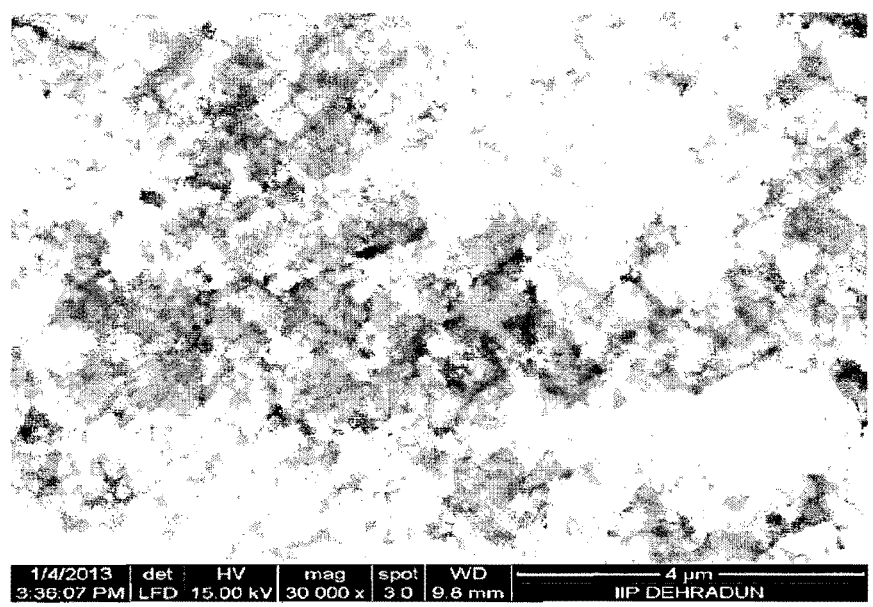
FIG. 4 SEM microgram of mesoporous $P/Al_2O_3$ catalyst.

The material was characterized using X-ray diffraction (XRD), Scanning electron microscopy (SEM), Nitrogen physisorption analysis. The adsorption isotherm for the P/Al2O3 catalyst found to be type IV with mean pore diameter 4 nm (FIG. 1) hysteresis curve of type H1 reveal that the of material is mesoporous in nature, which is further confirmed by the XRD pattern which shows (FIG. 2) a broad peak at 0.88° in low angle. The surface area observed for material was 225 m2/g, and total pore volume 0.48 cm3/g (FIG. 3). The SEM image of P//Al2O3 (P/Al=1) shows sponge like structure of the catalyst (FIG. 4).

Example—2

A typical synthesis procedure for the preparation of $P/Al_2O_3$ (P/Al=0.5) takes place as follows. Anhydrous Aluminum isopropoxide (4.1 g) was dissolved in 30 ml ethanol and 3.5 ml of concentrated nitric acid and 1 ml phosphoric acid was added into it. Finally 10 ml of ethanol was added again to the solution and kept for 10 h under vigorous stirring at 25° C. A second solution containing Poly(ethylene glycol)-block-poly(propylene glycol)-block-poly(ethylene glycol) (P123) 2 g was dissolved in 50 ml of ethanol solvent. Two solutions were mixed and stirred for few hours 3 hrs for homogenation and kept for drying slowly at temperature 60° C. for a period 48 hours. The obtained material was calcined at 700° C. for 6 h.

Figure 5:
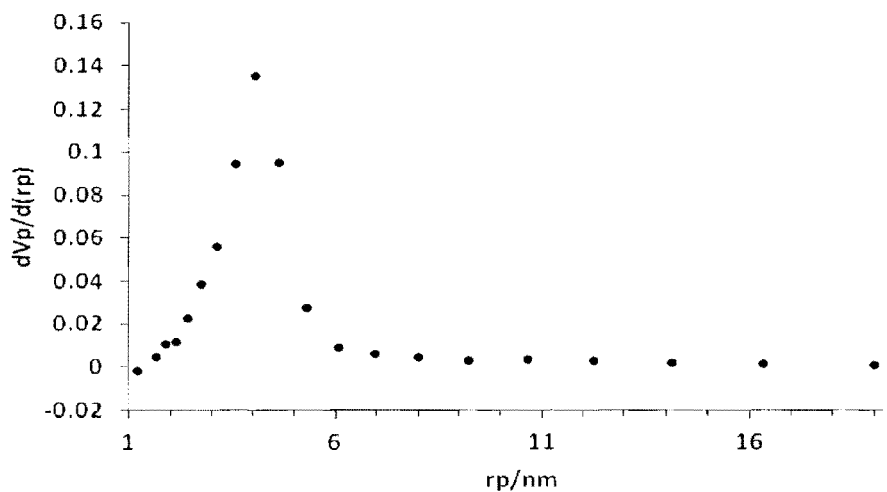
FIG. 5 shows BJH plot of mesoporous $P/Al_2O_3$ (P/Al=0.5) catalyst.
Figure 6:
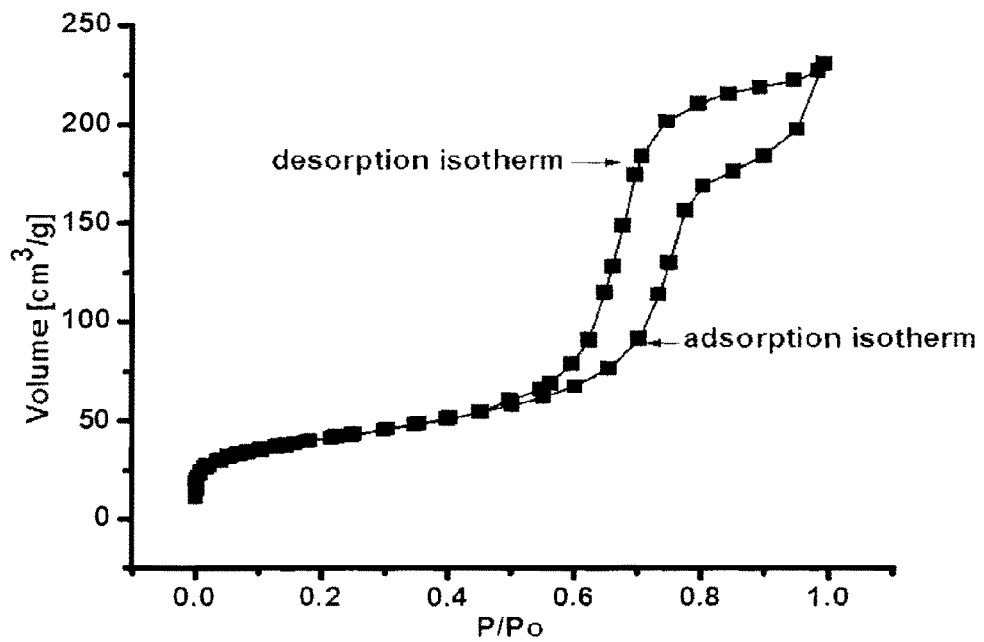
FIG. 6 Adsorption Desorption isotherm mesoporous of $P/Al_2O_3$ (P/Al=0.5) catalyst.
Figure 7:
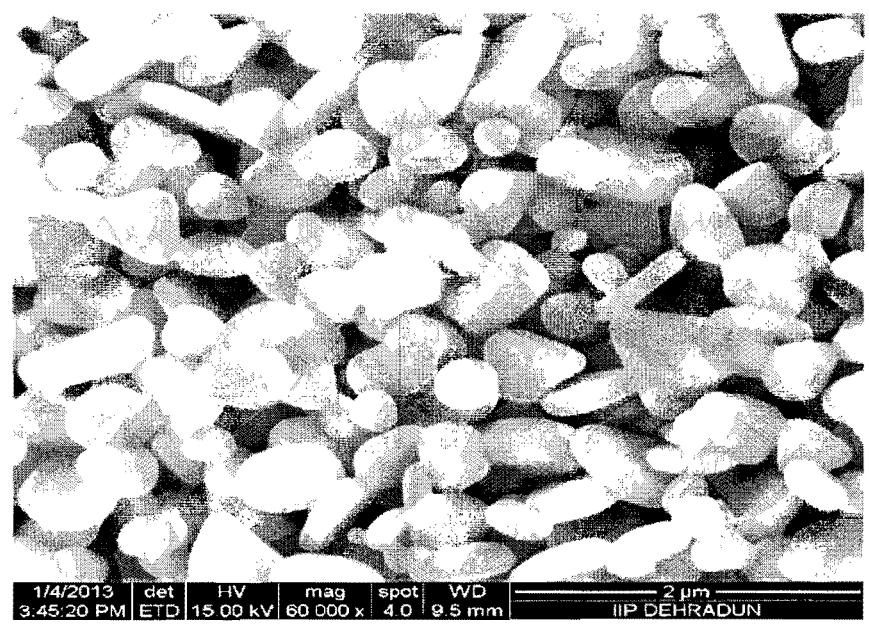
FIG. 7 SEM image of mesoporous $P/Al_2O_3$(P/Al=0.5) catalyst.

The material was characterized scanning electron microscopy (SEM), Nitrogen physisorption analysis. The adsorption isotherm for the $P/Al_2O_3$ catalyst found to be type IV with mean pore diameter 4 nm (FIG. 5), hysteresis curve of type H1 reveal that the of material is mesoporous in nature and the surface area observed for this catalyst 144.3 m²/g with total pore volume 0.35 cm³/g (FIG. 6). The SEM images of $P/Al_2O_3$ (0.5) catalyst shows quite homogeneously distributed mixture of particles (FIG. 7).

Example—3

This example describes the vapour phase dehydration of methanol by vapour phase reaction, He as carrier using different Al to P ratio of the catalyst. (Table-1)
Process Conditions
Catalyst: 0.15 g
Pressure: 1 atmosphere
Total flow=1 ml/min (LHSV=6.66 ml $g^{-1}$ $h^{-1}$)
Reaction time: 1 h

TABLE 1

| Catalyst ($P-Al_2O_3$) | Temperature (° C.) | Methanol Conversion (Mol %) | DME Selectivity (%) | DME Yield (%) |
|---|---|---|---|---|
| Al:P 1:1 | 300 | 94 | 100 | 94 |
| Al:P 1:0.5 | 300 | 36 | 95 | 35 |

Example—4

The example describes the effect of temperature on yield and selectivity of DME. The product analysis presented in Table-2.
Process Conditions:
Catalyst: 0.15 g
Al:P mole % in the catalyst 1:1.
Pressure: 1 atmosphere
Total flow=1 ml/h (LHSV=6.66 ml $g^{-1}$ $h^{-1}$)
Reaction time: 1 h

TABLE 2

| Catalyst ($P-Al_2O_3$) | Temperature (° C.) | Methanol Conversion (Mol %) | DME Selectivity (%) | DME Yield (%) |
|---|---|---|---|---|
| Al:P 1:1 | 200 | 46 | 100 | 46 |
|  | 250 | 68 | 100 | 68 |
|  | 300 | 94 | 100 | 94 |
|  | 350 | 77 | 97 | 75 |

Example—5

The example describes the effect of time on stream on methanol conversion to DME. The product analysis presented in Table 3:
Process Conditions:
Catalyst: 0.15 g
Al:P mole % in the catalyst=1:1
Pressure: 1 atmosphere
Total flow=1 ml/min (LHSV=6.66 ml $g^{-1}h^{-1}$)
Reaction temperature: 300° C.

TABLE 3

| Time in Hours | Conversion |
|---|---|
| 2 | 94.6 |
| 4 | 92.2 |

TABLE 3-continued

| Time in Hours | Conversion |
|---|---|
| 8 | 92.9 |
| 12 | 93.6 |
| 16 | 94.1 |
| 20 | 91.9 |
| 24 | 91.3 |
| 28 | 90.6 |
| 32 | 89.3 |
| 36 | 91.2 |
| 40 | 89.4 |

Example—6

The example describes the effect of Liquid hourly space velocity on yield and selectivity of DME. The product analysis presented in Table-4.
Process Conditions:
Catalyst: 0.15 g
Al:P mole % in the catalyst=1:1
Pressure: 1 atmosphere
Reaction temperature: 300° C.
Reaction time: 1 h

TABLE 4

| Catalyst (P/Al$_2$O$_3$) | LHSV (ml g$^{-1}$ h$^{-1}$) | Methanol Conversion (Mol %) | DME Selectivity (%) | Yield (%) |
|---|---|---|---|---|
| Al:P 1:1 | 2 | 88 | 99 | 87 |
|  | 6.66 | 94 | 100 | 94 |
|  | 9 | 84 | 100 | 35 |

Advantages of the Invention

The main advantages of the present invention are:
1. The process of the present invention converts methanol to DME in a single step with a single catalyst.
2. The process provides not only good conversion but also good selectivity for DME.
3. The process produces no by-product which is also a major advantage of this process.
4. The process does not need any addition reagent (such as chlorine, bromine etc.) to generate active species.
5. The catalyst is used in very low amounts.
6. The catalyst does not deactivate till 50 h with the reaction stream.

We claim:
1. A process for preparing a phosphorus containing mesoporous Al$_2$O$_3$ catalyst, wherein said process comprising the steps of:
 a) preparing a first solution by i) mixing aluminum isopropoxide in ethanol to give a mixture; ii) adding phosphoric acid, nitric acid and ethanol into the mixture to form a solution; and iii) stirring the solution for a period of 9-11 hrs at 25° C. to 35° C.;
 b) preparing a second solution by mixing Poly(ethylene glycol)-block-poly(propylene glycol)-block-poly (ethylene glycol) in ethanol;
 c) mixing two solutions consisting of the first solution and the second solution as obtained in steps (a) and (b) and stirring for a period of 3-5 hrs at 25° C. to 35° C. to give a third solution;
 d) obtaining a crude phosphorus containing mesoporous Al$_2$O$_3$ catalyst exclusively by drying the third solution at a temperature of 60°-150° C., for a period of 3-48 hrs; and
 e) calcining the crude phosphorus containing mesoporous Al$_2$O$_3$ catalyst at a temperature of 700° C. for 2-8 hrs, to obtain the phosphorus containing mesoporous Al$_2$O$_3$ catalyst.
2. The process as claimed in claim 1, wherein a mol ratio of Aluminium to Phosphorus in the catalyst is in the range of 0.5 to 5.
3. A process for vapour phase selective dehydration of methanol to dimethyl ether over phosphorus containing mesoporous Al$_2$O$_3$ catalyst as obtained by the process as claimed in claim 1, wherein the process comprises the steps of:
 placing the phosphorus containing mesoporous Al$_2$O$_3$ catalyst in between two quartz wool plugged in a center of a reactor;
 preheating the phosphorus containing mesoporous Al$_2$O$_3$ catalyst using helium at a temperature of 450° C.-600° C. for 2 hours; and
 contacting methanol over the phosphorus containing mesoporous Al$_2$O$_3$ catalyst after preheating at 1 atmospheric pressure, at a temperature of 150 to 350° C. for 1-50 h, at a liquid hourly space velocity of 2 ml g$^{-1}$ h$^{-1}$ to 10 ml g$^{-1}$ h$^{-1}$ to obtain dimethyl ether.
4. The process as claimed in claim 3, wherein a mol ratio of Aluminium to Phosphorus in the phosphorus containing mesoporous Al$_2$O$_3$ catalyst is in the range of 0.5 to 5.
5. The process as claimed in claim 3, wherein a conversion of methanol is in the range of 36 to 95%.
6. The process as claimed in claim 3, wherein a selectivity for dimethyl ether is 40 to 100%.

* * * * *